United States Patent [19]

Machulla et al.

[11] Patent Number: 4,473,544
[45] Date of Patent: Sep. 25, 1984

[54] RADIO-IODINE-LABELLED OMEGA PHENYL FATTY ACIDS

[76] Inventors: Hans-Jürgen Machulla, 290 Alfredstrasse, D-4300 Essen; Manfred Marsmann, 5600 Wuppertal MM; Klaus Dutschka, D-4300 Essen, all of Fed. Rep. of Germany

[21] Appl. No.: 398,008

[22] Filed: Jul. 14, 1982

Related U.S. Application Data

[63] Continuation-in-part of Ser. No. 209,048, Nov. 21, 1980, abandoned.

[30] Foreign Application Priority Data

Nov. 24, 1979 [DE] Fed. Rep. of Germany ....... 2947500

[51] Int. Cl.³ ..................... A61K 43/00; A61K 49/00
[52] U.S. Cl. .......................................... 424/1.1; 424/9
[58] Field of Search ..................... 424/1.1, 9

[56] References Cited

U.S. PATENT DOCUMENTS

| 2,580,459 | 1/1952 | Papa et al. | 424/4 X |
| 3,061,510 | 10/1962 | Numerof et al. | 424/1 |
| 4,202,874 | 5/1980 | Akerkar | 424/1 |
| 4,219,538 | 8/1980 | Sprinkle | 424/1 |
| 4,290,965 | 9/1981 | Stocklin et al. | 424/1 |
| 4,323,547 | 4/1982 | Knust et al. | 424/1 |

FOREIGN PATENT DOCUMENTS 69648 1/1983 European Pat. Off. ................ 424/1

OTHER PUBLICATIONS

Machulla et al., European Journal of Nuclear Medicine, 5, pp. 171–173 (1980).
Machulla et al., Journal of Nuclear Medicine, 19, No. 3, pp. 299–301 (1978).
Mattsson, International of Applied Radiation and Isotopes, May/Jun. 1976, pp. 319–323 (1978).
Wieland et al., J. Label. Comp. Radiopharmaceuticals, 16, 171 (1979).

Primary Examiner—Christine M. Nucker
Attorney, Agent, or Firm—Jon S. Saxe; George M. Gould; William H. Epstein

[57] ABSTRACT

Radio-iodine-labelled omega-phenyl fatty acid of the formula:

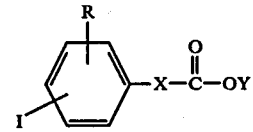

in which:
X is an alkylene group having from 6 to 20 carbon atoms; R is hydrogen or an alkyl or alkoxy group having 1 or 2 carbon atoms; Y is hydrogen, an alkali metal ion, alkaline earth metal ion or ammonium ion; and I is a radioactive iodine-123 or iodine-131 isotope which may be in the ortho- or para-position of the benzene nucleus, a process for the preparation of these radio-iodine-labelled phenyl fatty acids, and products containing them for scintigraphic examination of various organs of the body such as the heart and the liver.

12 Claims, No Drawings

4,473,544

RADIO-IODINE-LABELLED OMEGA PHENYL FATTY ACIDS

CROSS REFERENCE TO RELATED APPLICATIONS

This is a continuation-in-part of our earlier application Ser. No. 209,048 filed Nov. 21, 1980, abandoned.

BACKGROUND OF THE INVENTION

It is known that radio-iodine-labelled fatty acids are suitable for scintigraphic visualization of various organs such as the heart. Radioactive halogen-labelled fatty acids which accumulate most readily in the heart are those labelled with radio-iodine at the end of the chain, that is, at the omega-position. (*Journal of Nuclear Medicine,* 19:298 (1978).

Upon degradation via beta-oxidation, the remaining radioactive radical of omega-iodine fatty acids is present in the form of iodine which readily distributes throughout the blood and extracellular fluids. Consequently, scintigrams obtained utilizing these compounds do not represent the selective distribution of the radioactive fatty acid injected but rather the total radioactivity detected represents the sum distribution of both the radioactive fatty acid and the radioactive catabolite, iodide, throughout the entire blood and extracellular fluids. As a result, scintigrams of poor contrast are obtained such that fatty acid metabolism cannot be assessed quantitatively and marginal zones of infarct and ischemia regions cannot be clearly detected.

Chemical modification of fatty acids by terminal linkage of a phenyl radical has proved to have no influence on the biological activity of the novel agents of this invention, as compared to the activity of endogenous fatty acids. This is due to the fact that for these modified fatty acids, the hydrophobic character imparted by the long hydrocarbon chain and the hydrophilic center induced by the carboxylate group remain intact.

To be useful for scintigraphic applications for various organs of the body, it is necessary that radio-iodine-labelled omega phenyl fatty acids should readily accumulate in the organ to be imaged for diagnostic purposes. Biological transport mechanisms are of decisive importance. Transport of fatty acids throughout the blood, for example to the myocardial tissue, is effected by a transport protein, albumin, to which fatty acids are bound by both electrostatic and hydrophobic forces. Transport of fatty acids into cells utilizing them first requires the release of the fatty acid from the albumin protein complex. Therefore, the bond between the modified fatty acid and the albumin complex cannot be stronger than that of the bond between endogenous fatty acids and albumin. For transport across the cell membrane, the degree of liposolubility predetermined by the hydrophobic chain end is of decisive importance. Studies using alkane fatty acids have revealed that replacement of the hydrophobic methyl group by an iodine atom does not alter the biochemical and physiological properties of the fatty acid. There is also the difference with respect to these properties between an iodine-labelled phenyl fatty acid and endogenous fatty acids.

Diagnostic utilization of omega-iodine fatty acids is made feasible only through the use of a special correction process whereby the iodine-induced radioactive background can be subtracted from the total radioactivity detected. Accordingly, 30 minutes after administration of the labelled fatty acid, a known amount of radioactive iodide is injected as an internal standard. Knowing how much radioactive iodide was injected as an internal standard, it is then possible to calculate what proportion of the total radioactivity detected is due to the iodide-induced background and to correct the scintigram accordingly. In this way, scintigrams of good quality are obtained, such that localized rates of fatty acid catabolism in heart and liver tissue can be determined.

DETAILED DESCRIPTION OF INVENTION

We have now discovered radio-iodine-labelled omega-phenyl fatty acids, particularly p-$I_{123}$-omega-phenyl pentadecanoic acid and its use, to image body organs such as the heart and liver. Through the use of these novel agents, the disadvantages associated with the use of omega-iodine fatty acids, e.g., injecting radioactive iodide as an internal standard and making the necessary corrections, can be completely avoided. Degradation of radio iodine labelled phenyl fatty acids, via beta-oxidation of aromatic fatty acids, as was first discovered by Knoop in 1904, does not result in the release of free radioactive iodide, but rather results in the production of iodobenzoic or iodophenylacetic acid. These two products are rapidly and quantitatively excreted by the kidneys. Surprisingly, distribution of iodobenzoic and iodophenylacetic acid throughout the extracellular fluid does not occur.

In contrast thereto, radio-iodine-labelled omega-(para-aminophenyl) fatty acids, described by Wieland and Beierwalter (*Journal of Labelled Compounds and Radiopharmaceuticals,* 16:171 (1979) are physiologically unsuitable. Introduction of an amino group causes these fatty acids to carry a functional group at the hydrophobic chain end, which has both protic, and highly hydrophilic properties. Alteration of the hydrophobic character of the chain termini of phenyl fatty acids, has quite a number of consequences with respect to fatty acid transport from the blood into the cells:

Due to intermolecular and/or intramolecular head/tail interactions and corresponding salt formation with the amino group, the carboxy group is blocked, so that the native extended structure of the fatty acids is altered. Thus, binding of the fatty acids to the transport protein in a manner similar to that for endogenous fatty acids is impossible.

Upon binding of these modified fatty acids to the albumin, in addition to the electrostatic binding of the carboxyl group to the protein and the cumulative forces between the hydrophobic portions of the fatty acids and the albumin, bonding of the fatty acids between the amino group and acidic side chains of the protein is possible. Thus, the necessary release of the fatty acid from the albumin required for absorption of fatty acids by the heart tissue is made difficult.

The strength of the bond betweeen the fatty acid and the albumin is heavily influenced by the polarity alteration at the end of the fatty acid chain. For example, the binding to albumin of an alkane fatty acid when terminally labelled with bromine is of a different strength than when labelled with iodine. This phenomenon has been examined through equilibrium distribution studies whereby a protein solution is incubated with the halogen labelled fatty acid dissolved in heptane. While for the iodinated alkane fatty acid, the distribution between the organic and aqueous phases is found to be in a 1:1 ratio, for brominated fatty acids, due to the higher polarity of the bromine atom, the ratio was 1:4. As a consequence, when bromine-labelled alkane fatty acids are used, they tend to concentrate in the myocardial tissue and are therefore unsuitable for scintigraphic visualization of the myocardium.

Therefore, only in the case where polar, protic substituents such as amino groups are not present in the molecule, is scintigraphic visualization of the myocardium with the use of radio-iodine-labelled phenyl fatty acids possible.

The subject of the presently claimed invention is radio-iodine-labelled omega-phenyl fatty acid of the formula:

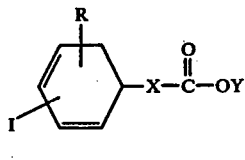 I in which

X is an alkylene group having from 6 to 20, preferably 12 to 16, carbon atoms; R is hydrogen or an alkyl or alkoxy group having 1 to 2 carbon atoms, preferably hydrogen; Y is hydrogen, an alkali metal ion, alkaline earth metal ion or ammonium ion; and I is a radioactive iodine-123 or iodine-131 isotope which may be in the ortho- or para-position of the benzene nucleus.

The radio-iodine-labelled omega-phenyl acids of the invention can be bound to albumin in the form of a complex.

The radio-iodine-labelled omega-phenyl fatty acids of formula I can be used to image various organs of the body for diagnostic purposes. The particular fatty acid of formula I particularly advantageous for imaging these organs is p-$I_{123}$-omega phenyl penta decanoic acid. These compounds can be utilized to image organs by conventional means such as through intravenously injection utilizing conventional compositions for such injections.

The fatty acids of formula I are effective imaging agents for all of the conventional organs of the body, particularly the heart and liver. Through the use of these fatty acids, one is able by conventional scintigraphic means to effectively image the organs of the human body for diagnostic purposes.

The radio-iodine-labelled phenyl fatty acids of this invention can be prepared for example as follows: 0.5 mg of phenyl fatty acid in 500 ul of a glacial acetic acid/sulfuric acid mixture (10/1) are reacted within 15 minutes at 120 C. with from 10 to 40 ul of the intended activity of radioactive iodide in 0.01N sodium hydroxide solution in the presence of 10 ul of chloroform and 50 ul of freshly melted sodium nitrite; the desired isomer of the radio-iodine-labelled phenyl fatty acid is separated from the reaction mixture by means of high-pressure liquid chromatography.

Products for scintigraphic examination of the heart and liver can be prepared with the use of the above-radio-iodine-labelled omega-phenyl fatty acids by dissolving the phenyl fatty acids in amounts of from 1 ng to 100 ug in 1 to 2 ml of blood serum, a 6% human serum-/albumin solution.

An example of utilizing such products are then utilized for imaging various organs of the body such as the heart or the liver as follows:

1 ml of the injection solution containing about 1.5 mCi of radio-iodine-labelled phenyl fatty acid, particularly p-$I_{123}$-omega-phenyl pentadecanoic acid, is administered by intravenous injection to a patient positioned before the head of a gamma camera in a manner suitable for the kind of scintigraphic picture desired.

On degradation via beta-oxidation of the iodinated phenyl fatty acid of the invention, the radioactive residue produced is not iodide, but rather iodinated benzoic or iodinated phenylacetic acid. These products are known to be rapidly excreted from the body via the kidneys. Tests in mice have proven that the residual activity in the blood is 2% of the injected dose per gram of blood. This results in a distribution ratio of heart to blood of maximally 20:1; in contrast, the hitherto known omega-iodine fatty acids, under conditions of identically good heart accumulation, attain a ratio of only about 6:1.

While the accumulation in the liver is not significantly influenced by the position of the iodine on the benzene nucleus, differences in heart accumulation, depending on the position of the iodine on the benzene nucleus, are observed. In mice heart, the omega-paraiodine-phenyl fatty acids, at a rate of 38% of injected activity per gram of heart tissue, attain the highest degree of accumulation, while all otherwise substituted compounds, although clearly accumulating in the heart, do not attain more than about 20% of the injected dose per gram.

A further advantage of using iodinated phenyl fatty acids resides in the lack of radiation strain on the thyroid. The level of radioactivity present in mouse stomach is used as an indicator of strain on the thyroid gland. When using radio-iodine-labelled alkane fatty acids, the radioactivity rises to about 12% within ½ hour; however, when using the radio-iodine-labelled phenyl fatty acids of formula I, the radioactivity is maintained constant at about 1%. This is due to the fact that on degradation radioactive iodide is formed which then accumulates in the thyroid. The production of radioactive iodide occurs only from the degradation of radio-iodine-labelled alkane fatty acids, not from the degradation of radio-iodine-labelled phenyl fatty acids. The following example illustrates the invention illustrates the method of preparing the iodinated omega-phenyl fatty acids of formula I.

EXAMPLE 1

Five hundred ug of phenylpentadecanoic acid are dissolved in 500 ul of a mixture of glacial acetic acid and concentrated sulfuric acid (10:1), and introduced into a test tube having a capacity of 5 ml. Five to 10 ul of a 0.01N NaOH solution containing radioactive iodide having an activity of from 20 to 100 mCi is added. After the addition of about 500 ug of sodium nitrite, the tube is immediately closed and heated for 15 minutes at 120 C. with agitation to produce an isomer mixture of the 30% o-$I_{123}$-omega phenyl fatty acid and 70% of p-$I_{123}$-omega phenyl fatty acid.

The iodinated product is purified by high-pressure liquid chromatography with simultaneous separation of the individual iodine isomers. For this purpose, the reaction solution is diluted with 500 ul of eluant and injected onto a column (length 25 cm, diameter 1 cm) packed with alkylated silica gel (grain size 10 um). The eluant is a mixture of methanol, glacial acetic acid and water (96/4/0.5). The product fraction is evaporated, dissolved in 1 ml of eluant and again injected. After the first separation, the product fraction is evaporated, dissolved in 1 ml of eluant and again injected. After the first separation, the product fraction still contains traces of non-iodinated phenyl fatty acid. These traces, however, considerably reduce the solubility of the product in the injection solution; by repeating the separation, this difficulty is overcome. The product fraction so obtained is further-purified by passing it over a 10 um silica gel column (length 25 cm, diameter 0.3 cm) with the use of a mixture n-heptane and glacial acetic acid (99.65/0.35) as eluant.

According to this process, iodophenyl fatty acids containing alkylene groups of 6, 12, 14 and 18 carbon atoms, and radiochemical yields of from 65 to 75% in an isomer mixture of 30% of ortho- and 70% of para-iodophenyl fatty acid are prepared.

What is claimed is:

1. A radio-iodine-labelled ω-phenyl fatty acid of the formula:

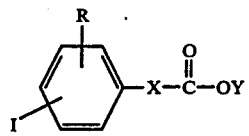

wherein X is an alkylene group having from 6 to 20 carbon atoms; R is hydrogen; Y is hydrogen, an alkali metal ion, alkaline earth metal ion or ammonium ion, and I is a radioactive iodine-123 or iodine 131 isotope which may be in ortho- or para-position of the benzene nucelus.

2. The radio-iodine labelled omega-phenyl fatty acid of claim 1 wherein Y is hydrogen.

3. The radio-labelled omega fatty acid of claim 2 wherein said acid is p-I$_{123}$-omega-phenyl-pentadecanoic acid.

4. A method of imaging organs of the body comprising intravenously injecting an effective amount of a composition comprising a compound of the formula:

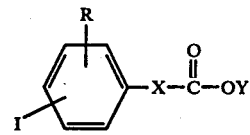

wherein X is an alkylene group having from 6 to 20 carbon atoms; R is hydrogen; Y is hydrogen, an alkali metal ion, alkaline earth metal ion or ammonium ion; and I is a radioactive iodine-123 or iodine-131-isotope which may be in ortho- or para-position of the benzene nucleus.

5. The method of claim 4 wherein said organ is the liver.

6. The method of claim 4 wherein said organ is the heart.

7. The method of claim 1 wherein said compound is p-I$_{123}$-omega-phenyl-decanoic.

8. The method of claim 7 wherein said organ is the heart.

9. The method of claim 7 wherein said organ is the liver.

10. The fatty acid of claim 1 wherein I is in the para position.

11. The method of claim 4 wherein Y is hydrogen.

12. The method of claim 11 wherein I is in the para position.

* * * * *